US012029840B2

(12) United States Patent
 Engeln

(10) Patent No.: US 12,029,840 B2
(45) Date of Patent: Jul. 9, 2024

(54) DEVICE FOR DRAINING AWAY WASTE WATER

(71) Applicant: FRESENIUS MEDICAL CARE DEUTSCHLAND GMBH, Bad Homburg (DE)

(72) Inventor: Florian Engeln, Laubach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1037 days.

(21) Appl. No.: 16/960,324

(22) PCT Filed: Jan. 8, 2019

(86) PCT No.: PCT/EP2019/050281
§ 371 (c)(1),
(2) Date: Jul. 7, 2020

(87) PCT Pub. No.: WO2019/137885
PCT Pub. Date: Jul. 18, 2019

(65) Prior Publication Data
US 2020/0368419 A1    Nov. 26, 2020

(30) Foreign Application Priority Data

Jan. 11, 2018  (DE) ..................... 10 2018 000 146.7

(51) Int. Cl.
*A61M 1/16*        (2006.01)
(52) U.S. Cl.
CPC .......... *A61M 1/168* (2013.01); *A61M 1/1654* (2013.01)
(58) Field of Classification Search
CPC ............................ A61M 1/168; A61M 1/1654
See application file for complete search history.

(56) References Cited

U.S. PATENT DOCUMENTS 3,515,280 A * 6/1970 Parker ................... B01D 29/41
                                                    210/314
3,752,318 A * 8/1973 DeRouen ........... B01D 17/0211
                                                    210/522

(Continued)

FOREIGN PATENT DOCUMENTS

| DE | 102009038571 A1 | 2/2011 |
| EP | 2286850 A1 | 2/2011 |
| JP | 2016106801 A | 6/2016 |

OTHER PUBLICATIONS

International Search Report and Written Opinion issued in corresponding International Patent Application No. PCT/EP2019/050281 (with English translation of International Search Report) dated Mar. 22, 2019 (10 pages).

(Continued)

*Primary Examiner* — Monica E Millner
(74) *Attorney, Agent, or Firm* — Kilyk & Bowersox, P.L.L.C.

(57) ABSTRACT

The invention relates to a device for discharging wastewater, in particular used or spent dialysate, comprising a plurality of line connections 3, 4, 5 for connecting wastewater lines, in particular wastewater lines of dialysis machines. The device according to the invention is designed as a part which can stand on the bottom of a basin. Sufficient stability can be achieved on account of the weight (gravitational force) of the device alone, without it being necessary to secure the device. Recontamination is prevented effectively in that the line connections 3, 4, 5 are in fluid connection with at least one inflow line, the lower end of which is arranged so as to be spaced apart from the bottom, such that a free-fall distance is formed. In a preferred embodiment, a casing 1 surrounds the at least one inflow line 6, 7, 8.

(Continued)

Figure 1:
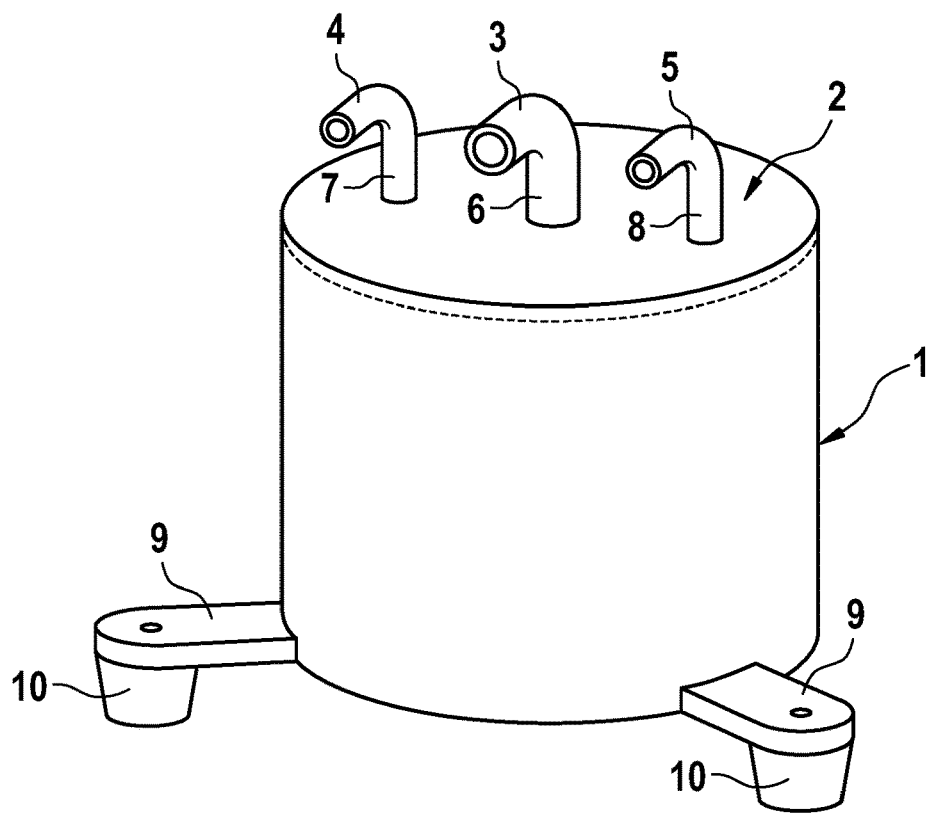

The casing 1 forms a splash guard in the form of a hood such that the wastewater, which emerges from the inflow lines 6, 7, 8 under relatively high pressure, cannot reach the surroundings.

18 Claims, 4 Drawing Sheets

(56) References Cited

U.S. PATENT DOCUMENTS

| | | | | |
|---|---|---|---|---|
| 4,176,684 A | | 12/1979 | Kelso et al. | |
| 4,431,534 A | * | 2/1984 | Gordon | B01D 17/0214 210/923 |
| 4,449,969 A | * | 5/1984 | Schweizer | F16M 11/22 600/580 |
| 4,824,562 A | * | 4/1989 | Carson | B01D 17/0214 210/170.07 |
| 4,955,873 A | * | 9/1990 | Rajlevsky | F16M 11/22 248/97 |
| 5,217,038 A | * | 6/1993 | Pinder | A61M 1/63 137/562 |
| 5,309,670 A | * | 5/1994 | Bates | A01G 9/08 248/346.11 |
| 6,267,901 B1 | * | 7/2001 | Franklin | B01D 17/04 210/104 |
| 6,494,869 B1 | * | 12/2002 | Hand | A61M 1/63 141/330 |
| 7,290,557 B1 | | 11/2007 | Bowman | |
| 7,481,243 B2 | * | 1/2009 | Michaels | F04F 5/10 137/892 |
| 8,025,173 B2 | * | 9/2011 | Michaels | A61M 1/882 220/495.08 |
| 10,369,258 B2 | * | 8/2019 | Hensler | A61M 1/60 |
| 10,513,842 B2 | * | 12/2019 | Quesada | A61M 1/70 |
| 2002/0000402 A1 | * | 1/2002 | Dillon | A61M 1/16 210/232 |
| 2005/0161562 A1 | | 7/2005 | DiMaggio | |
| 2019/0106872 A1 | * | 4/2019 | Grover | E03C 1/102 |

OTHER PUBLICATIONS

International Preliminary Report on Patentability issued in corresponding International Patent Application No. PCT/EP2019/050281 (with English translation) dated Jul. 14, 2020 (11 pages).

* cited by examiner

C-D:

DEVICE FOR DRAINING AWAY WASTE WATER

This application is a National Stage Application of PCT/EP2019/050281, filed Jan. 8, 2019, which claims priority to German Patent Application No. 10 2018 000 146.7, filed Jan. 11, 2018.

The invention relates to a device for discharging wastewater, in particular used or spent dialysate, comprising a plurality of line connections for connecting wastewater lines, in particular wastewater lines of dialysis machines.

The use of medico-technical appliances in a clinical setting often requires used or spent fluids to be discharged into a drain. These fluids are hereafter referred to as wastewater.

The known dialysis machines have wastewater tubes for discharging used and/or spent dialysate, for example. It is important to note that, when discharging the dialysate, there must be no direct fluid connection between the wastewater tube and the wastewater line system, as otherwise there is a risk of contamination. This can be achieved by not directly connecting the free end of the wastewater tube to a wastewater line system, but instead maintaining a specified free-fall distance. The free end of the wastewater tube can be arranged at a specified height above the bottom of a wastewater basin (sink), for example.

In practice, the problem arises of adequately guiding and securing the wastewater line while still maintaining a specified free-fall distance. This problem occurs in both chronic and acute dialysis. In particular, guiding and securing a plurality of wastewater lines when using a plurality of dialysis machines at one station has been found to be problematic.

In the field of sanitary engineering or household equipment, the principle of creating a free-fall distance is known from U.S. Pat. No. 7,290,557 B1. However, the problem of contamination of medical fluids or medico-technical devices does not arise in the field of household equipment or sanitary engineering. U.S. Pat. No. 7,290,557 B1 discloses a connecting piece for connecting a service water tube of a dishwasher to the downpipe of a service water line system. The connecting piece, which is rigidly connected to a downpipe by a screw connection or an insertion connection, comprises a pipe portion through which the service water flows into the downpipe. Said pipe portion comprises a lateral opening for better aeration and/or ventilation. The connecting piece and the downpipe are of substantially the same diameter. The connecting piece is preferably made of plastics material.

A disadvantage is that the connecting piece only allows a single service water tube to be connected to a downpipe. In order to connect a plurality of service water tubes, a plurality of connecting pieces is required, corresponding branches being required on the downpipe, to which branches the connecting pieces can be connected. This requires more space.

Moreover, fixing a service water line, for example the service water line of a washing machine, to the basin edge of a sink is known in the field of household equipment.

The object of the invention is to simplify the discharge of wastewater, in particular of used or spent dialysate, without the risk of contamination arising.

This object is achieved according to the invention by the features of claim 1. The dependent claims relate to preferred embodiments of the invention.

The device according to the invention for discharging wastewater is intended in particular for medical appliances, in particular dialysis machines, in order to allow medical fluids to be discharged. The preferred use is therefore not in building services engineering (sanitary or architectural engineering) in technical installations for wastewater disposal. The device for discharging wastewater, in particular used or spent dialysate, comprises a plurality of line connections for connecting wastewater lines, in particular wastewater lines of dialysis machines. The device can comprise, for example, two, three or more than three line connections, such that the wastewater lines of a plurality of appliances, in particular dialysis machines, can be connected.

The basic concept of the invention consists in designing the device for discharging wastewater according to the invention as apart which can stand on the bottom of a basin. The device thus forms a supporting foot which is easy to handle and can stand on the bottom of a basin. The device allows a plurality of wastewater lines to be connected while requiring only limited space. Said device can also absorb lateral tensile forces of the connecting lines.

Sufficient stability can be achieved on account of the weight (gravitational force) of the device alone, without it being necessary for the device to be secured to the edge of a basin for example. The device can therefore be placed in the centre of the basin without being secured further.

Contamination is thereby prevented effectively in that the line connections are in fluid connection with at least one inflow line, the lower end of which is arranged so as to be spaced apart from the underside or footprint of the part which can stand on the bottom of the basin, such that a free-fall distance is formed. The length of the free-fall distance is determined by the height of the lower end of the inflow line or the dimensions of the device. Owing to the free-fall distance, the wastewater can also be discharged under relatively high pressure, for example between 2 and 4 bar, without the risk of contamination.

In a preferred embodiment, the device for discharging wastewater comprises a casing which surrounds the at least one inflow line. The casing forms a splash guard in the form of a hood such that the wastewater, which emerges from the inflow line under relatively high pressure, cannot reach the surroundings. Sufficient stability can be achieved on account of the weight of the casing alone.

The casing preferably comprises a plurality of laterally protruding supporting legs, by means of which the device can be securely laterally supported against the bottom of the basin such that the device itself cannot tilt or fall over if the dead weight alone is not enough for sufficient stability. The contact surface is therefore many times greater than the diameter of the wastewater lines. However, additional supporting legs do not need to be provided.

In a particularly preferred embodiment, the supporting legs comprise supporting feet such that the underside of the casing is arranged so as to be spaced apart from the bottom of the basin. This embodiment has the advantage that a free-fall distance for splashed water running down the wall of the casing is also created. The length of the free-fall distance, i.e. of the spacing between the lower edge of the casing and the bottom, is determined by the dimensions of the supporting feet. The supporting feet allow wastewater to flow away freely under the casing on all sides.

In a further embodiment, the device comprises a lid on which the line connections are provided. The lid and the casing can be produced either as two rigidly interconnected parts or as a single piece. The lid is preferably a circular or dish-shaped part, whereas the casing is preferably a hollow cylindrical part. The lid and the casing can, however, also be of other shapes. For example, the lid can be hemispherical and the casing can be cylindrical.

The at least one inflow line can be designed and arranged in various ways, for example the at least one inflow tube can be a cannula. The cannula is preferably a straight cannula, but can also be curved. The cannula does not need to be arranged perpendicularly, but can also be arranged obliquely.

The upper end of the inflow line is preferably designed as a connecting piece for connecting a hose line. The connecting piece is preferably angled such that the outflow line can be guided in from the side and laterally connected.

In a preferred embodiment, each line connection is in fluid connection with one inflow line, respectively. It is, however, also possible for all the line connections to be in fluid connection with just one inflow line. Individual line connections can also be in fluid connection with a plurality of inflow lines.

The inflow lines can be of the same length, such that they are at the same spacing from the underside of the part which can stand on the bottom of the basin, or the inflow lines can be of different lengths, such that they are at different spacings from the underside of the part which can stand on the bottom of the basin. The inflow lines can be of the same diameter or different diameters. The length and the diameter of the inflow lines can thus be individually adjusted to the different flow rates or the different pressures of individual appliances.

The lid and/or the casing preferably consist of stainless steel, which is easy to clean and/or disinfect. If the lid and/or the casing consist of stainless steel, the device also has sufficient dead weight to provide sufficient stability. The two stainless steel parts can be easily interconnected, for example welded, but can also be adhesively bonded to one another. It is therefore not necessary to manufacture the splash guard in one piece. However, if the supporting legs ensure sufficient stability, the lid and/or the casing can in principle also be made of plastics material.

In practice, certain uses involve relatively high fluxes such that the wastewater, in particular the dialysate, enters the free-fall distance from the inflow line at a high flow speed, for example 6 m/s, which can cause undesired splashing.

In a further embodiment, the inflow line or at least one of the inflow lines comprises a diffuser or is designed as a diffuser, such that the flow of fluid is slowed down. The associated line connection, instead of the inflow line, can comprise a diffuser or be designed as a diffuser. In a preferred embodiment, the inflow line or at least one of the inflow lines has a cross section that widens towards the lower end. The cross section can increase over the entire length or over only part of the length; for example, it can increase only at the lower end part of the inflow line. Owing to the lower flow speed of the wastewater, in particular the dialysate, undesired splashing is at least decreased or reduced.

Embodiments of the device according to the invention for discharging wastewater are described in greater detail below, with reference to the drawings.

Figure 2:
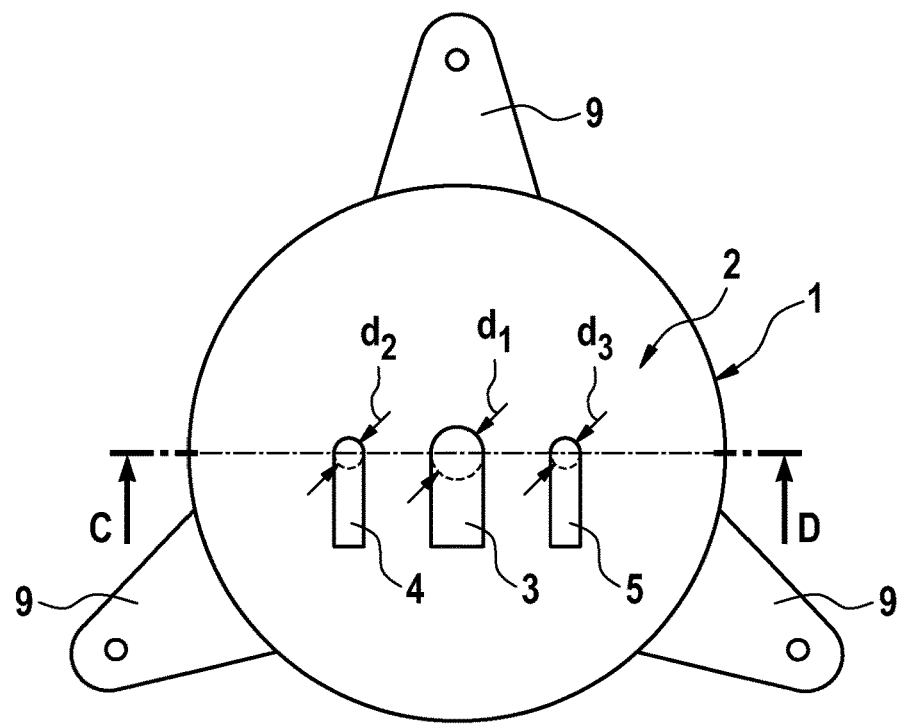
Figure 3:
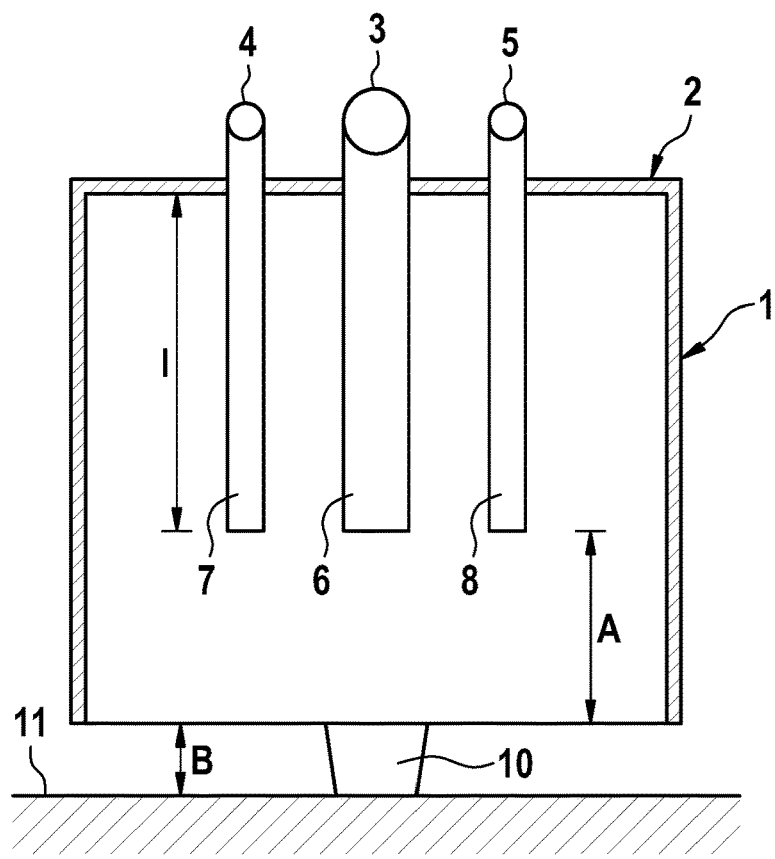
Figure 4:
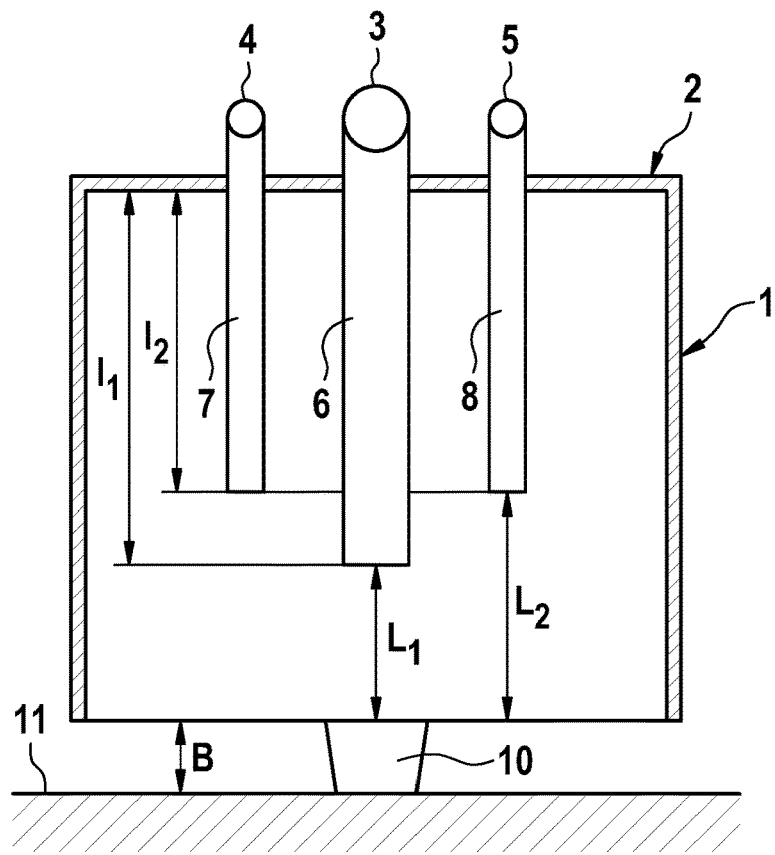
Figure 5:
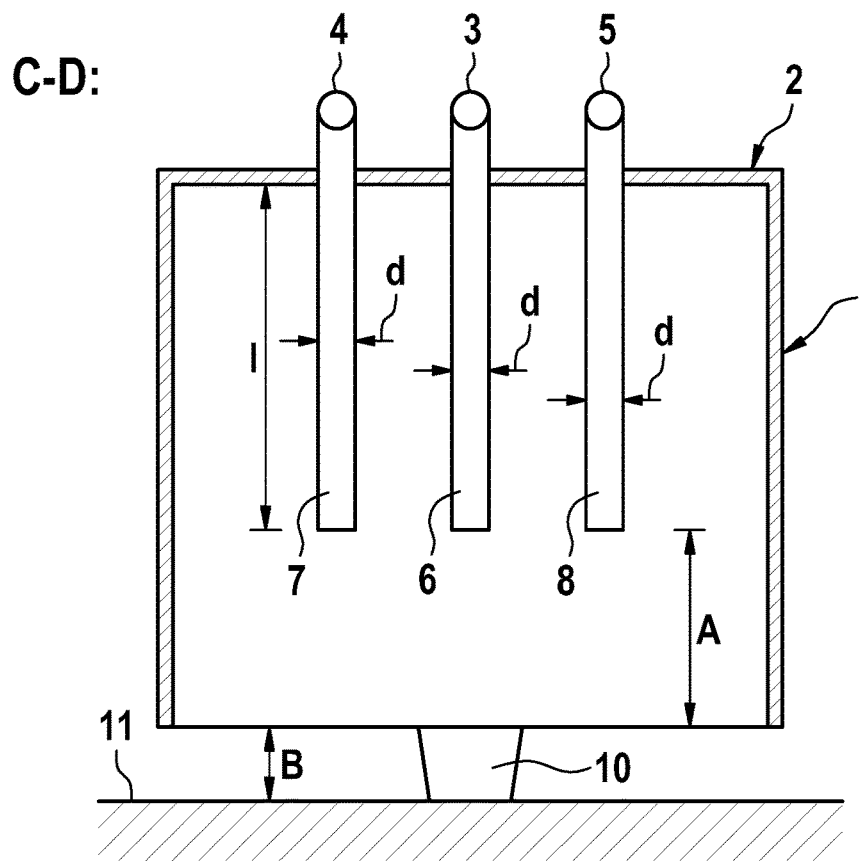
Figure 6:
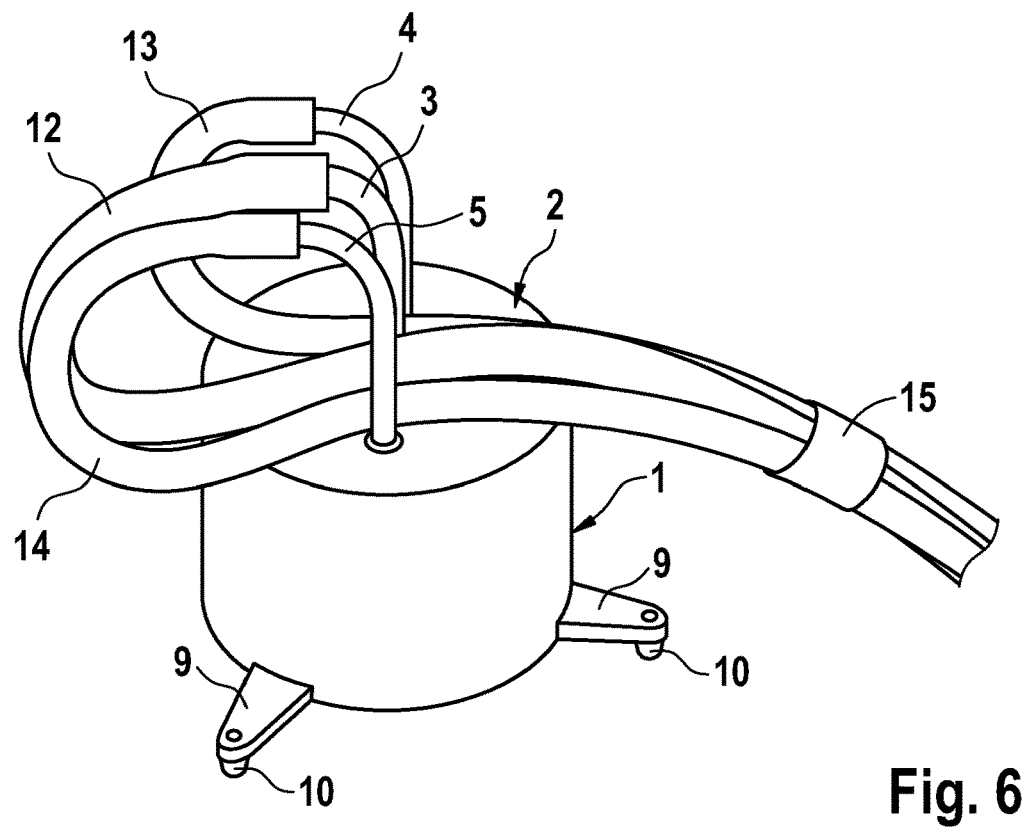
Figure 7:
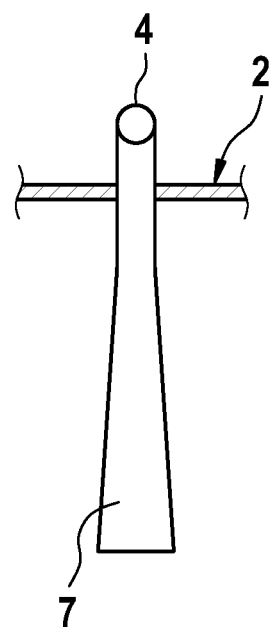

In the drawings:

FIG. 1 is a perspective view of an embodiment of the device according to the invention, FIG. 2 is a plan view of the device from FIG. 1, FIG. 3 is a section through the device from FIG. 1, FIG. 4 is a section of a second embodiment of the device, FIG. 5 is a section of a third embodiment of the device, FIG. 6 is a perspective view of the device, the wastewater tubes being connected to the device, and FIG. 7 is a further embodiment of an inflow line.

FIG. 1 is a perspective view of the device according to the invention for discharging wastewater. FIG. 2 is a plan view of the device. The device comprises a hollow cylindrical casing 1, the top of which is connected to a circular lid 2. The casing 1 and the lid 2 consist of stainless steel and are interconnected, in particular welded, so as to form a hood-shaped body which can also be referred to as a bell.

Three mutually spaced line connections 3, 4, 5 are provided on the lid 2 for connecting hose lines (not shown). The line connections 3, 4, 5 are designed as connecting pieces, onto which wastewater tubes of medico-technical devices, in particular dialysis machines, can be slid in a fitted manner. Hose line couplings or the like can also be provided instead of the connecting pieces, for easily connecting and removing the hose lines. The connecting pieces 3, 4, 5 are angled at 90° relative to the axis of the cylindrical casing 1, such that the wastewater tubes can be slid on laterally. The central connecting piece 3 has an external diameter $d_1$ which is greater than the external diameters $d_2$, $d_3$ of the outer connecting pieces 4, 5, such that a wastewater tube having a larger diameter can be slid, in a fitted manner, onto the central connecting piece 3. The connecting pieces are formed in a single piece with inflow lines 6, 7, 8 which extend inside the casing 1. The inflow lines 6, 7, 8 comprising the connecting pieces 3, 4, 5 preferably consist of stainless steel (FIG. 3).

FIG. 3 is a section through the casing 1. The inflow lines 6, 7, 8 are straight cannulas which extend downwards from the lid 2. The central inflow line 6 extends along the longitudinal axis, and the two outer inflow lines 7, 8 extend adjacently to the longitudinal axis of the cylindrical casing 1. The inflow lines 6, 7, 8 are of the same length 1. The lower ends of the inflow lines 6, 7, 8 are arranged so as to be spaced apart from the lower edge of the casing 1, such that a free-fall distance for the wastewater emerging from the inflow lines 6, 7, 8 is formed. This spacing is denoted by reference sign A in FIG. 3.

The casing 1 comprises a plurality of supporting legs 9. In the present embodiment, three supporting legs 9 are provided (tripod), which extend radially outwards from the lower edge of the casing 1. The supporting legs 9 each comprise a supporting foot 10. The supporting feet 10 can be rubber feet that are secured to the supporting legs 9, for example screwed thereto, and by means of which feet the device stands securely on the bottom and cannot slip or tilt. Since the device stands on the bottom using the supporting feet 10, the lower edge of the casing 1 is spaced apart from the bottom 11. This spacing is denoted by reference sign B in FIG. 3.

The device for discharging wastewater is placed on the bottom 11 of a wastewater basin, for example a sink. During operation of the device, the wastewater emerges from the inflow lines 6, 7, 8 under relatively high pressure, which can be 3 bar, and splashes onto the bottom 11 of the basin. Recontamination is prevented by the free-fall distance, which is of a length L=A+B. The wastewater can flow under the casing 1 and into the basin on all sides, and can run off into the drain of the basin. Splashed water is retained by the lid 2 and the casing 1 and runs off the wall of the casing 1. Recontamination by the splashed water that is running off is prevented in that the lower edge of the casing 1 is spaced apart from the basin bottom 11, as a result of which a free-fall distance of length L=B is formed. The splashed water can run along the entire periphery of the lower edge of the casing 1, or drip down and flow under the casing into the drain.

FIG. 4 is a section of a second embodiment of the device, which differs from the first embodiment in that the inflow lines 6, 7, 8 are of different lengths $l_1$, $l_2$. The mutually corresponding parts are provided with the same reference signs. The length $l_1$ of the central inflow line 6 is longer than that of the outer inflow lines. This results in free-fall distances of different lengths $L_1$, $L_2$.

FIG. 5 is a section of a third embodiment of the device, which differs from the first embodiment in that the inflow lines 6, 7, 8 are of the same diameter d and the same length l. The mutually corresponding parts are provided with the same reference signs.

FIG. 6 is a perspective view of the device for discharging service water, the waste water tubes 12, 13, 14 of a medico-technical device (not shown) being connected to the connecting pieces 3, 4, 5. The central wastewater tube 12 is of a greater tube diameter than the outer wastewater tubes 13, 14. The wastewater tubes 12, 13, 14 laterally connected to the connecting pieces 3, 4, 5 are guided back over the lid 2 in a semicircular curve and bound together into a tube bundle by means of a touch-and-close fastener 15 or the like. The device is therefore also used for guiding and securing the wastewater tubes 12, 13, 14. The wastewater tubes 12, 13, 14 can, however, also extend to the other side, without forming a semicircular curve.

Safe, stable discharge for a plurality of medico-technical devices at the same time can be achieved by means of the "discharge bell" according to the invention. The discharge bell can be placed in any sink. Guiding and securing the wastewater tubes ensures controlled drainage of wastewater, the free-fall distances preventing recontamination of the relevant wastewater tube. Due to the simple geometric shape, the discharge bell can be cost-effectively produced as a welded component without high demands on the manufacturing engineering, in particular the dimensional accuracy. The discharge bell can be freely accessed without tools and is easy to clean and/or disinfect. Since the wastewater can flow downwards on all sides, the wastewater can be easily seen in the basin, and the visual character thereof can therefore be monitored. The discharge bell can be used not only in medical technology, but also universally in all fields when fluids are to be discharged into a drain.

FIG. 7 shows an inflow line 7 of the device for discharging wastewater, in particular dialysate. The inflow line 7 is designed as a diffuser and has a cross section that increases towards the end, such that wastewater is decelerated and enters the free-fall distance at a lower speed, for example at 1 m/s or less. In this way, undesired splashing is at least decreased or reduced.

The invention claimed is:

1. A device for discharging wastewater, comprising:
a plurality of line connections configured to connect to wastewater lines;
at least one inflow line in fluid connection with the plurality of line connections, the at least one inflow line comprising a lower end;
a casing that surrounds the at least one inflow line, the casing comprising an outer wall and a lower edge that defines an opening; and
a plurality of support legs laterally protruding from the outer wall, wherein
the device for discharging wastewater is configured to stand on a bottom of a basin, and
the lower end of the at least one inflow line is arranged so as to be spaced apart from the lower edge of the casing such that the lower end of the at least one inflow line is disposed within the casing and spaced apart from the opening and a free-fall distance is formed.

2. The device for discharging wastewater according to claim 1, wherein the plurality of support legs radially protrude from the outer wall.

3. The device for discharging wastewater according to claim 1, wherein each support leg of the plurality of support legs comprises a respective support foot such that the lower edge of the casing is configured to be spaced apart from the bottom of the basin when the device is within the basin.

4. The device for discharging wastewater according to claim 1, wherein the casing is a hollow cylindrical part.

5. The device for discharging wastewater according to claim 1, further comprising a lid at an upper end of the casing, wherein the plurality of line connections are provided on the lid.

6. The device for discharging wastewater according to claim 5, wherein the lid is a circular part.

7. The device for discharging wastewater according to claim 1, wherein the at least one inflow line is a cannula, each line connection of the plurality of line connections is at the upper end of the cannula, and each line connection of the plurality of line connections is a respective connecting piece for connecting a respective hose line.

8. The device for discharging wastewater according to claim 7, wherein each respective connecting piece is angled.

9. The device for discharging wastewater according to claim 1, wherein the at least one inflow line is a plurality of inflow lines and each line connection of the plurality of line connections is in fluid connection with a respective inflow line of the plurality of inflow lines.

10. The device for discharging wastewater according to claim 9, wherein all of the inflow lines of the plurality of inflow lines are of the same length, such that the respective lower end of each of the plurality of inflow lines are at the same spacing from the lower edge of the casing.

11. A device for discharging wastewater, comprising:
a plurality of line connections configured to connect to wastewater lines;
a plurality of inflow lines in fluid connection with the plurality of line connections, each inflow line of the plurality of inflow lines comprising a respective lower end;
a casing that surrounds the plurality of inflow lines, the casing comprising a lower edge that defines an opening; and
an underside configured to stand on a bottom of a basin, wherein
each inflow line of the plurality of inflow lines is configured to discharge fluid through the opening of the casing,
the respective lower end of each inflow line of the plurality of inflow lines is arranged so as to be spaced apart from the underside of the device such that a free-fall distance is formed, and
the inflow lines of the plurality of inflow lines are of different lengths, such that the respective lower end of each inflow line of the plurality of inflow lines is at a different spacing from the underside of the device.

12. The device for discharging wastewater according to claim 9, wherein all of the inflow lines of the plurality of inflow lines are of the same diameter.

13. A device for discharging wastewater, comprising:
a plurality of line connections configured to connect to wastewater lines;
a plurality of inflow lines in fluid connection with the plurality of line connections, each inflow line of the plurality of inflow lines comprising a respective lower end;
a casing that surrounds the plurality of inflow lines, the casing comprising a lower edge that defines an opening; and
an underside configured to stand on a bottom of a basin, wherein
each inflow line of the plurality of inflow lines is configured to discharge fluid through the opening of the casing,
the respective lower end of each inflow line of the plurality of inflow lines is arranged so as to be spaced apart from the underside of the device such that a free-fall distance is formed, and the inflow lines of the plurality of inflow lines are of different diameters.

14. The device for discharging wastewater according to claim 5, wherein the casing and/or the lid consists of stainless steel.

15. The device for discharging wastewater according to claim 1, wherein the at least one inflow line comprises a diffuser configured to slow down a flow of fluid.

16. The device for discharging wastewater according to claim 15, wherein the at least one inflow line has a cross section that widens towards the lower end.

17. The device for discharging wastewater according to claim 1, wherein the plurality of line connections are configured to connect to wastewater lines that convey used dialysate.

18. The device for discharging wastewater according to claim 1, wherein the plurality of line connections is connected to wastewater lines of at least one dialysis machine.

* * * * *